United States Patent [19]

Yamashiro

[11] Patent Number: Plant 5,865

[45] Date of Patent: Jan. 27, 1987

[54] PEACH TREE, SUMMER LADY

[75] Inventor: Hideo P. Yamashiro, Parlier, Calif.

[73] Assignee: The Burchell Nursery, Inc., Modesto, Calif.

[21] Appl. No.: 707,489

[22] Filed: Mar. 1, 1985

[51] Int. Cl.[4] ..... A01H 5/00

[52] U.S. Cl. ..... Plt./43

[58] Field of Search ..... Plt./43

*Primary Examiner*—James R. Feyrer

*Attorney, Agent, or Firm*—Worrel & Worrel

[57] ABSTRACT

A new and distinct variety of peach tree, denominated "Summer Lady", producing freestone fruit similar to that of the O'Henry peach tree but ripening one week to ten days earlier under the same cultural practices.

1 Drawing Figure

BACKGROUND OF THE NEW VARIETY

The present invention relates to a new and distinct variety of peach tree to be known as the "Summer Lady", and more particularly to such a peach tree which is broadly characterized by its similarity to the O'Henry variety of peach tree (U.S. Plant Pat. No. 2,964).

The new variety is a single scaffold mutation of the O'Henry peach tree from which it is distinguished and characterized as to novelty by bearing fruit which ripens approximately one week to ten days earlier, which is more nearly globose than that of the O'Henry and which displays less green fruit ground color and a more uniform and brighter overall red skin coloration than the O'Henry at maturity.

ORIGIN

The mutated scaffold was discovered by Hideo P. Yamashiro while propping limbs before harvest of O'-Henry peach trees. The new mutation was first observed in July of 1982 in a commercial orchard of O'-Henry peach trees located at 17281 East Adams Avenue, Parlier, in Fresno County, Calif. The above orchard of O'Henry peach trees is currently eight years of age and is owned and was owned at the time of the discovery by Hideo P. Yamashiro.

ASEXUAL REPRODUCTION

The new variety was grafted onto existing peach stock in February of 1984, at the direction of the applicant. The resultant asexually reproduced trees are located at 17281 East Adams Avenue, Parlier, Fresno County, Calif. Floral buds on the one-year old scion-wood used in grafting produced several fruits in the same year of grafting. These fruit clearly demonstrate that the repropagated trees are true to the original mutation in all observable aspects.

DISTINCTIVE CHARACTERISTICS

The new variety of peach tree is an early ripening mutation of the O'Henry peach tree. The O'Henry ripens in early August in the Reedley/Parlier growing area of Fresno County, Calif., Aug. 3, 1984 in the orchard of discovery. The new variety ripens from one week to ten days earlier than the O'Henry, July 24, 1984 in the orchard of discovery. The characteristics of the tree of the new variety are very similar to those of the O'-Henry. The tree is of moderate vigor and very productive. The fruit shape is slightly different from that of the O'Henry. The fruit of the O'Henry are slightly compressed laterally while fruit of the new variety are generally more globose. Fruit coloration of the new variety is also slightly different from that of the O'Henry. The fruit of the O'Henry is usually highly blushed red with exposed blush surfaces often turning a dark burgundy color at maturity. The new variety is also highly blushed red, 90% to 100% of the fruit surface, but does not turn as dark as the O'Henry on the exposed blush surfaces at maturity. This characteristic, in addition to a less green fruit ground color, tends to give the new variety a more uniform and brighter overall red skin coloration than the parent O'Henry peach tree.

BRIEF DESCRIPTION OF THE DRAWING

The accompanying drawing is a color photograph of four mature peaches viewed from four right angularly related points of view: a single peach divided along its suture line to show its flesh; a twig with ten characteristic leaves; and a single leaf viewed from the back thereof, all of the subject variety.

DETAILED DESCRIPTION

The following description of the "Summer Lady" Peach variety was made on July 28, 1984 from fruit of firm commercial maturity grown at Parlier, Calif. Color definitions are from the *Dictionary of Color,* by Maerz and Paul, published 1950.

TREE

Size: Growth rate and character indicate that the ultimate tree size will be medium. No mature specimen has been observed. The descriptions of the mature habit are extrapolations.

Figure: Upright, spreading. Vase-shaped with form and density determined by pruning.

Vigor: Medium.

Productivity: Very productive.

Regularity of bearing: Regular. Hardy for California, Central Valley conditions.

Trunk:

- *Thickness.*—Medium.
- *Surface texture.*—Medium.
- *Color of mature bark.*—Grey, Plate 8-C-9 to Greyish Brown, Plate 8-C-10.
- *Lenticels.*—Numerous.

Branches:

- *Size.*—Medium.
- *Surface texture.*—Smooth to medium.

*Color of mature branches.*—Brown, Plate 7-A-11.
*Color of immature branches.*—Green, Plate 19-I-5.
*Lenticels.*—Medium in size and numerous.

Leaves: Measurements are from leaves growing at mid-point of vigorous current season shoots.
*Average length.*—18.1 cm.
*Average width.*—4.1 cm.
*Size.*—Moderately large.
*Form.*—Lanceolate, tip acuminate.
*Color.*—Upper Surface — Dark green, Plate 24-H-5. Lower Surface — Grey-green, Plate 21-F-6.
*Leaf margin.*—Finely crenate, occasionally doubly so. Edge slightly undulate.
*Petiole.*—Medium in length, 1.0 to 1.1 cm. Thickness — 2 mm. Color — Yellow-Green, Plate 19-J-5, petiole groove darker green, Plate 20-J-6.
*Stem glands.*—Reniform type, 2 to most commonly 4 in number. Alternate in position, above medium in size. Located most commonly at or very slightly below leaf edge basal margin. Color — Light Green, Plate 20-I-5.
*Stipules.*—Medium size, 7 to 8 mm. in length. Usually two at base of petiole, early deciduous. Color — Light Green, Plate 20-I-6, at times tinged with red.

Flower buds: Medium size, average for species. Conic in form, moderately plump. Buds free from stem and covered with short grey pubescence. Buds hardy under usual San Joaquin Valley growing conditions.

Flowers: Flowers of "Summer Lady" are similar in phenology to original O'Henry. Bloom is large in size, showy form. Light Pink petal color. In comparison with other commercial peach varieties, slightly late in bloom.
*Date of first bloom.*—Mar. 2, 1984 in Parlier, Calif.
*Date of full bloom.*—Mar. 7, 1984.

FRUIT

Maturity: Described at firm, full commercial maturity, July 28, 1984.
*First pick.*—July 24, 1984.
*Last pick.*—July 30, 1984.

Size: Medium to large.
*Uniformity.*—Uniform.
*Average axial diameter.*—66 mm.
*Average suture diameter.*—74 mm.
*Average cheek diameter.*—72 mm.

Form: Uniform. Axial aspect generally globose with one protruding suture lip. Lateral aspect slightly oblate to globose. Fruit slightly unsymmetrical with one side usually larger.
*Suture.*—A narrow line from base to apex, and extending beyond the apex 5 to 7 mm. Suture shallow and inconspicuous at mid-fruit, becoming slightly deeper and folded 10 to 15 mm. from apex and 15 to 18 mm. from base. Suture coloration blends with general fruit skin color.
*Ventral surface.*—Generally rounded with one side lipped near base or apex, and unequal.
*Stem cavity.*—Shallow, somewhat flaring, round to oval in basal aspect. 10 to 12 mm. in depth. 20 to 25 mm. in length. 18 to 20 mm. in width.
*Base.*—Rounded to slightly truncate. Most commonly at right angle to fruit axis.
*Apex.*—Short, rounded to slightly depressed. Pitsil point apical and depressed.
*Stem.*—Medium length, 10 to 12 mm. Thickness, 2 to 3 mm. Stem coloration Light Green, Plate 20-J-5.

Skin:
*Thickness.*—Medium.
*Texture.*—Medium.
*Tendency to crack.*—None observed.
*Pubescence.*—Light, short.
*Color.*—Red, Plate 4-J-10, to Dark Red, Plate 6-K-9, blush coloration. Ground color Yellow, Plate 10-K-2. Blush coloration usually covers 90% to 100% of fruit surface. Yellow ground color usually visible only on stem end. Blush color uniform and regular, occasionally a few darker dapples over basal shoulder or along suture area.

Flesh:
*Color.*—Yellow, Plate 9-K-4. No red coloration at edge of skin.
*Surface of pit cavity.*—Bright Red, Plate 6-K-9.
*Amygdalin.*—Slight to lacking.
*Juice.*—Abundant when fully ripe.
*Flavor.*—Good, mild, well balanced.
*Aroma.*—Moderate, pleasant.
*Texture.*—Fine textured, melting.
*Fibers.*—Medium length, fine, Light Yellow, Plate 10-J-3.
*Ripening.*—Even.
*Eating quality.*—Very good.

Stone:
*Adhesion.*—Full freestone. Some fibers cling to stone along base and basal ventral suture.
*Size.*—Medium. Averge length — 33 mm. Average width — 26 mm. Averge thickness — 18 mm.
*Fibers.*—Few, medium in length.
*Form.*—Roughly oval.
*Base.*—Slightly oblique to ventral suture.
*Hilum.*—Narrow, oval.
*Apex.*—Rounded, with cuspidate tip.
*Sides.*—Very nearly equal.
*Surface.*—Heavily grooved and pitted with grooves over basal shoulder converging basally. Grooves over apical shoulder parallel to edge of stone.
*Pits.*—Both circular and elongated types appearing laterally in mid-stone area.
*Ventral edge.*—Medium thick and winged, with wings most prominent over basal area.
*Dorsal edge.*—Full, heavily grooved with jagged edges. Groove deepest over basal shoulder. Dorsal edge moderately eroded over apical shoulder.
*Color.*—Brown, Plate 13-D-9. Stained Red-Purple, Plate 7-C-4, especially basally and along ventral suture.
*Tendency to split.*—None observed.

Use: Fresh market for both local and long distance markets.

Keeping quality: Good.

Resistance to insects and disease: No particular susceptibilities noted.

Shipping quality: New variety has not been shipped commercially in quantity.

SUMMARY

This new and distinct variety of peach tree is characterized by its similarity in tree and fruit to that of the O'Henry vareity of peach tree (U.S. Plant Pat. No. 2,964) from which it is a single scaffold mutation and from which it is distinguished and characterized as to novelty by bearing fruit which ripens approximately 1 week to 10 days earlier than the fruit of the O'Henry variety and which is distinguished from the fruit of the O'Henry in being more nearly globose and by displaying less green fruit ground color and a more uniform, brighter overall red skin coloration than that of the O'Henry.

Although the new variety of peach tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having described my new variety of peach tree, what I claim as new and desire to secure by Plant Letters Patent is:

1. A new and distinct variety of peach tree, substantially as illustrated and described, characterized by similarity in tree and fruit to that of the O'Henry vareity of peach tree (U.S. Plant Pat. No. 2,964), from which it is a single scaffold mutation and from which it is distinguished and characterized as to novelty by bearing fruit which ripens approximately one week to ten days earlier than fruit of the O'Henry variety and which is distinguished from the fruit of the O'Henry in being more nearly globose and by displaying less green fruit ground color and a more uniform and brighter overall red skin coloration than that of the O'Henry at maturity.

* * * * *

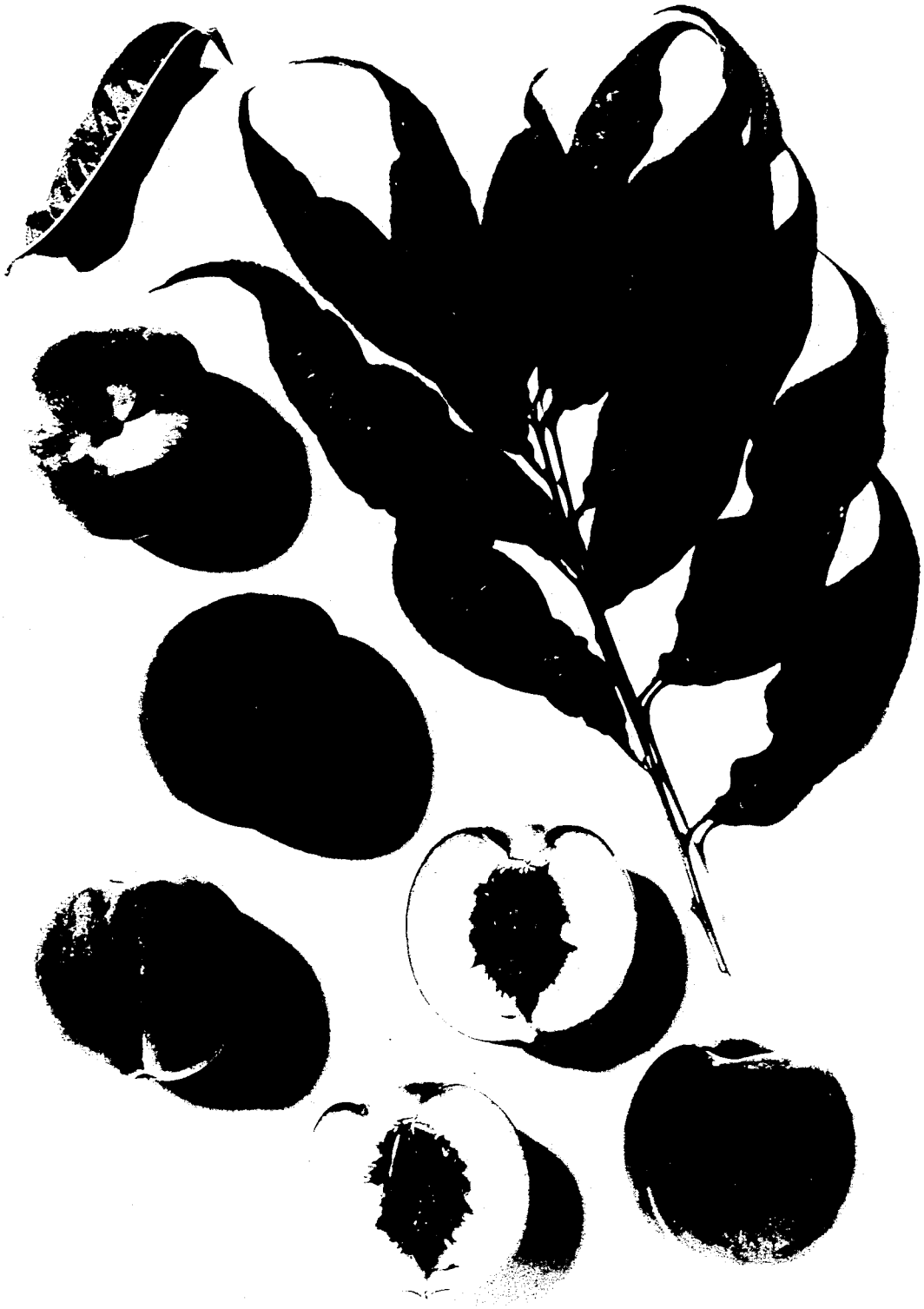

UNITED STATES PATENT AND TRADEMARK OFFICE

CERTIFICATE OF CORRECTION

PATENT NO. : PP 05865

DATED : January 27, 1987

INVENTOR(S) : Hideo P. Yamashiro

It is certified that error appears in the above-identified patent and that said Letters Patent is hereby corrected as shown below:

Column 3, line 67, delete "Pitsil" and substitute ---Pistil---.

Column 4, line 32, delete "Averge" and substitute ---Average---.

Column 4, line 33, delete "Averge" and substitute ---Average---.

Signed and Sealed this

Twelfth Day of May, 1987

*Attest:*

DONALD J. QUIGG

*Attesting Officer*

*Commissioner of Patents and Trademarks*